United States Patent [19]
Fuerst et al.

[11] Patent Number: 5,837,645
[45] Date of Patent: Nov. 17, 1998

[54] MATERIALS AND METHODS UTILIZING A TEMPORARY VISUAL INDICATOR

[76] Inventors: Ronnie S. Fuerst, 112 Turtle Cove Ct., Lexington, S.C. 29072; Richard Melker; Christopher D. Batich, both of 3733 N.W. 40th St., Gainsville, Fla. 32606

[21] Appl. No.: 674,069

[22] Filed: Jul. 1, 1996

Related U.S. Application Data

[60] Continuation of Ser. No. 388,402, Feb. 14, 1995, Pat. No. 5,532,029, which is a division of Ser. No. 242,517, May 13, 1994, abandoned, which is a continuation-in-part of Ser. No. 61,412, May 13, 1993, Pat. No. 5,523,075.

[51] Int. Cl.$^6$ .............................. B41M 5/00; B32B 1/06; A61K 31/34; A61K 7/42
[52] U.S. Cl. ........................ 503/201; 273/363; 273/418; 424/59; 428/34.1; 428/35.7; 428/36.92; 428/321.1; 428/321.5; 514/470; 549/308
[58] Field of Search ............................ 563/201; 273/363, 273/418; 424/59; 428/34.1, 35.7, 36.92, 321.1, 321.5; 514/470; 549/308

[56] References Cited

U.S. PATENT DOCUMENTS

| | | | |
|---|---|---|---|
| 2,366,759 | 1/1945 | Thomas et al. | 424/59 |
| 2,496,270 | 2/1950 | Coler | 424/59 |
| 2,948,657 | 8/1960 | Siccama | 424/59 |
| 4,678,658 | 7/1987 | Casey et al. | 424/10.3 |
| 4,954,544 | 9/1990 | Chandaria | 524/111 |

FOREIGN PATENT DOCUMENTS

| | | |
|---|---|---|
| 0218732 | 4/1987 | European Pat. Off. . |
| 0388543 | 9/1990 | European Pat. Off. . |
| 0471105 | 2/1992 | European Pat. Off. . |
| 2115825 | 7/1972 | France . |
| 2356431 | 1/1978 | France . |
| 3206204 | 1/1983 | Germany . |
| 2050829 | 1/1981 | United Kingdom . |

OTHER PUBLICATIONS

Naigai Ink Mfg., (Dec. 1976) Abstract for Japanese Patent No. 51046446, Database WPI, Derwent Publications, Ltd., London, Great Britain.

Club Kosumechitsukusu KK, (Feb. 2, 1993) Abstract for Japanese Patent No. 05025030, Patent Abstracts of Japan vol. 17, No. 309.

*Primary Examiner*—Shelley A. Dodson
*Attorney, Agent, or Firm*—Saliwanchik, Lloyd & Saliwanchik

[57] ABSTRACT

This invention relates to novel compositions containing temporary visual indicators and methods for using these compositions. Specifically, this invention relates to a sunscreen composition containing an indicator that is visible when the substance is applied to the skin, but becomes invisible shortly after application. The continued presence of the indicator allows the indicator to be reactivated temporarily to the visible form so that a user can verify the presence of the sunscreen. The visible indicator ensures that the sunscreen is applied evenly and completely to the area to be protected, but becomes invisible so as not to interfere with the action of the sunscreen or discolor the skin.

6 Claims, No Drawings

MATERIALS AND METHODS UTILIZING A TEMPORARY VISUAL INDICATOR

CROSS-REFERENCE TO A RELATED APPLICATION

This is a continuation of application Ser. No. 08/388,402, filed Feb. 14, 1995 now U.S. Pat. No. 5,532,029; which is a division of application Ser. No. 08/242,517, filed May 13, 1994, now abandoned; which is a continuation-in-part of application Ser. No. 08/061,412 filed May 13, 1993, now U.S. Pat. No. 5,523,075.

BACKGROUND OF THE INVENTION

The potentially harmful effects of overexposure to solar radiation are now well-documented. These harmful effects range from the discomfort of minor sunburn to increased incidences of serious disorders such as skin melanomas. A variety of methods for avoiding overexposure to the sun's rays have been devised. The use of hats, protective clothing, and other physical barriers to block radiation is common. A wide variety of chemical compounds are also available which can be used to block or absorb certain constituents of solar radiation. Such chemical compounds are widely used in suntan compositions. Such suntan compositions may be formulated to absorb a major portion of the incident radiation and screen the user from the sun's rays or they may be formulated to allow most of the radiation to pass through. The consumer can choose an appropriate level of sunscreen protection.

One problem frequently encountered by sunscreen users pertains to the difficulty in achieving complete and uniform protection. Uneven or incomplete application of sunscreen may result from the difficulty in applying lotion to hard-to-reach areas of the body such as the middle of the back. The back is not only hard to reach, but it is also hard to see, and therefore, it is often difficult to tell accurately where sunscreen has been applied. Even for portions of the body which are easy to reach and to see, it is often difficult to know where sunscreen has been applied because it is either clear as it is applied or it quickly becomes clear as it is rubbed into the skin. Thus, a common problem encountered by sunbathers or others who use sunscreen is the occurrence of localized areas of sunburn caused by the incomplete or uneven application of sunscreen. Such overexposure to the sun's rays can result in unattractive, uneven tanning and, more importantly, can lead to serious skin disorders if the overexposure is prolonged or particularly severe.

Another common problem faced by sunscreen users is knowing whether the sunscreen that had been applied at an earlier time is still present. Sunscreens are often formulated to be water-proof or water-resistant, but there are no guarantees as to just how water-resistant. Therefore, after several trips to and from the water, sunbathers cannot be certain their sunscreen has not washed away leaving them unprotected from the sun.

The subject invention provides, for the first time, an easy means for the sunscreen user to know exactly where sunscreen has, and has not, been applied and whether already applied sunscreen is still present. The technology of the subject invention can also be utilized in other situations where it is desired to know where a particular material has been applied. Clear lacquers, varnishes or sprays formulated with the temporary visual indicator of the subject invention allows the user to ensure that an area is adequately covered by these materials by providing a temporary color guide for the user during their application. The temporary visual indicator of the subject invention formulated with pesticides, herbicides or fertilizers guides the user in accurate and complete application of these materials to a treated area. In preparing for surgery or other medical procedure, it is often necessary or desirable to apply a disinfecting, medicated, or analgesic lotion or spray to a particular area of the patient. It is advantageous, or critical, to know precisely where that lotion or spray has been applied. The temporary visual indication of the subject invention ensures the entire surgical area is disinfected.

An adhesive compound which undergoes color changes upon application is described in Chandaria, U.S. Pat. No. 4,954,544. The indicator affecting the color change in '544 enhances the physical characteristics of the composition by contributing to the improved flow and adhesion of the glue. The indicator also adds to the economy of the product by allowing the glue to be formulated with less adhesive compound. Unlike the indicator in '544, the temporary visual indicator of the present invention is incorporated into a material exclusively to provide a visual guide for the application of that material to a surface. Until now there has been no accurate means for knowing the precise location where lotions or other like materials have been applied.

BRIEF SUMMARY OF THE INVENTION

The subject invention concerns novel methods and compositions useful for providing temporary visual indication of the location to which a lotion or other material has been applied. The materials and methods of the subject invention are specifically exemplified with reference to sunscreen, but a person of ordinary skill in the art would appreciate that the teachings of the subject invention can be readily applied to other technologies.

Specifically exemplified herein are sunscreen compositions which contain a visual indicator allowing the sunscreen user to know exactly where the sunscreen has been applied. Advantageously, the visual indicator provided according to the subject invention is visible only temporarily and disappears within a short period of time so as not to interfere with the transparent nature or activity of the sunscreen. As described herein, the compositions of the subject invention can be formulated by a person skilled in the art, using the teachings of the instant invention, to permit the indicator to remain visual for a period of time appropriate for the particular application. For example, in the case of sunscreen the indicator may remain visual for about 15 seconds to 2 minutes or more after the initial application of the lotion and for only 30 seconds to 1 minute upon reactivation of the indicator.

In a preferred embodiment of the subject invention, a sunscreen is formulated with a compound which is visible at a first pH and invisible at a second pH. The sunscreen is formulated at said first pH, wherein the indicator is visible but, upon application to the skin, the sunscreen changes pH, within a short period of time, to said second pH, wherein the indicator can no longer be seen. The indicator can be reactivated to its visible form by temporarily returning the pH of the lotion already applied to the skin to the first pH to verify the continued presence of the sunscreen. As a specific example, the visual indicator useful according to the subject invention can be phenolphthalein, which is pink and can be seen at a pH of 9.0 and above, but is invisible or colorless at a pH below 8.5. The sunscreen composition containing phenolphthalein can be formulated with a volatile base, e.g., ammonia, such that the composition has a pH greater than 9.0 when applied, but becomes neutral after a short period of time because of the evaporation or degradation of the base. As used herein, reference to degradation of the base includes neutralization and a chemical conversion or reaction such as that which takes place when water absorbs carbon dioxide thereby reducing the OH⁻concentration and, consequently, the pH. The $CO_2$ may be supplied directly or simply be absorbed from ambient air. Thus, the phenolphthalein is initially visible, but within a short period of time will disappear. The phenolphthalein in the sunscreen can be reactivated temporarily by reapplying a base.

The technology can be applied to other situations or compositions where a visual indicator is needed temporarily.

DETAILED DESCRIPTION OF THE INVENTION

The subject invention concerns novel methods and compositions useful for providing a temporary visual indication of the location to which a lotion or other material has been applied. As used herein, the term lotion includes creams, gels, ointments and solutions. In the preferred embodiment, the lotion is a sunscreen. A temporary visual indicator formulated with a sunscreen has the advantage of allowing the user to apply the sunscreen evenly over the areas to be protected as well as completely so that no areas are left unprotected. Sunscreen products should be applied at a certain thickness to be most effective. The color intensity of the indicator of the subject invention can vary with the amount of product applied to the skin. Therefore, a color guide on the side of a bottle of sunscreen can be used to provide the user with a color match system to assure an appropriate amount of sunscreen is being applied to provide the desired protection. Reactivation of the indicator with a disclosing solution, for instance, in a spray, allows the user to check whether the sunscreen is still present on the skin and protecting the sunbather from the harmful rays of the sun. The visual indicator disappears after a matter of minutes so as not to interfere with the sunscreen's activity or stain or discolor the skin or clothing.

A temporary visual indicator formulated with all types of suntan products provides a similar advantage. Suntan products are not only those compositions that prevent sunburn, e.g., sunscreen, but also are those compositions that cause or create a tan. Suntan lotions or oils which cause tanning formulated with a temporary visual indicator ensure the user an even tan making sure all areas of the skin are covered. The temporary indicator formulated with a product that creates an artificial tan provides the user with a visual guide so that the "tan" is applied completely. Additionally, the color intensity of the indicator varies with the amount of product applied to the skin therefore, a user is certain to apply the "tan" evenly.

The temporary visual indicator of the subject invention formulated into other compounds also results in advantageous compositions and methods. For example, a temporary visual indicator formulated with topical dermatologicals ensures that the medication is evenly and completely dispensed over the entire affected area. The color intensity of the indicator varies with the amount of medication applied. Therefore, the indicator serves to guarantee the proper amount of medication is applied to the treated area. A temporary visual indicator formulated with a surgical scrub ensures that the area being disinfected is completely scrubbed. Surgical scrubs often contain iodine as a disinfecting agent. The iodine in the scrub stains the skin on contact and serves as a color guide for application as well as a disinfecting agent to ensure the area is completely scrubbed. Iodine, however, has fallen into disfavor for use in surgical scrubs. Iodine has been found to support the growth of certain bacterial pathogens. Additionally, iodine has been found to be toxic to dermal cells thereby impeding the healing of surgical incisions. The temporary visual indicator specifically exemplified in the present invention is not toxic to dermal cells. Furthermore, the temporary nature of the indicator provides that no color is left on the skin to interfere with surgical marks to be used in the procedure.

The visual indicators of the subject invention can be used to improve the utility of a variety of products. For example, the accuracy of a spray is often unreliable; therefore, a temporary visual indicator formulated with an antibacterial spray is quite advantageous because the temporary visual indicator makes certain that the entire infected area is treated. Similarly, a temporary visual indicator formulated with dental sealants ensures that the entire surface area of the tooth is covered and adequately sealed. In ophthalmic solutions, a temporary visual indicator verifies adequate administration of the solution to the eye, yet does not interfere with sight after the indicator turns colorless.

The temporary visual indicator of the subject invention can be formulated with other products which require proper and complete coverage of a surface. A temporary indicator formulated with paints, varnishes, or lacquers guarantees adequate coverage of a surface. When applying a second coat of paint, the temporary visual indicator ensures that fresh paint is applied to the entire painted surface so that paint will not dry unevenly or blotchy. In working with clear finishes such as lacquers or varnishes, it is often difficult to tell which areas have or have not been covered. The temporary indicator provides a color guide while the finish is being applied which then rapidly disappears so that the clear finish properties of the compound are retained. Car polish or other polishes formulated with a temporary visual indicator ensure complete coverage of the car with the polish, but do not stain or discolor the finish of the car.

The temporary visual indicator of the subject invention formulated with certain products ensures that these products are accurately applied. The color guide provided by the temporary visual indicator formulated with a grease compound not only ensures that an area is adequately greased, but also ensures that other components are not soiled by the grease compound. Teflon sprays and coatings which are difficult to remove if misapplied are accurately applied when formulated with a temporary visual indicator.

A temporary visual indicator formulated into protective sealants ensures that an area is completely sealed and protected. Fabrics and carpets are often treated to protect against stains. These textiles sometimes have intricate weaves or deep naps and it is difficult to be sure that all areas of the fabric are adequately treated. A temporary visual indicator formulated in protective sprays provides the user with a color guide for applying the protectant so that the user is sure that even recessed areas of a weave are protected from stains. A temporary visual indicator formulated into sealants such as waterproofing agents for wooden decks allows the user to be sure that the deck in fully sealed. The temporary nature of the indicator, however, ensures that the sealant will not mask the grain or stain the wood.

In one embodiment of the subject invention a temporary visual indicator can be utilized in paramilitary drills or games in order to provide a means for temporarily marking a player. Specifically, projectiles ("paint balls") can be filled with a temporary visual indicator (instead of paint) such that a person or object struck with the projectile will be marked with the indicator as the projectile breaks. The temporary visual indicator, formulated as described herein, would remain visible for a designated period of time upon release from the projectile. The marking thus applied will gradually disappear and, in the case of a paramilitary game, the player can return to the game once the color has disappeared. This ensures that the player "sit out" for the appropriate period before rejoining the game. Thus, the player can return to the game, unmarked, without having to change clothes or uniforms. At the end of the game it is possible to determine how many times an individual has been struck with a projectile by applying a base to the clothing in order to re-visualize the indicator. Technology for manufacturing "paint balls," including filling the outer shell with a liquid, is well known in the art. Therefore, with the benefit of the applicants' disclosure, the temporary visual indicator of the subject invention can be readily incorporated into such "paint balls."

A temporary visual indicator formulated with pesticides, herbicides or fertilizers ensures adequate treatment of all areas with the compound. Uneven greening of a plant caused by disproportionate coverage of the plant with a pesticide is avoided. The indicator formulated with a pesticide for in-home use does not stain floors, walls or woodwork to which the pesticide is applied. The presence of the indicator not only ensures that the pesticide is adequately applied, but also ensures that the pesticide is accurately applied. The color guide provided by the temporary indicator guarantees that children's toys, house plants or pet dishes lying on the floor are not mistakenly sprayed with the pesticide. Pots, pans, utensils, and food items within cabinets and drawers being treated will likewise be protected from the effects of stray pesticide. Items that are mistakenly sprayed are immediately identifiable and can be washed to remove the pesticide. A base can be applied to the washed item to verily no residual pesticide is present.

Herbicides formulated with the temporary visual indicator allow for selective application of the product to plants. The herbicide N-phosphomethyl glycine, (glyphosate), is a broad-spectrum, non-selective herbicide that kills virtually all vegetation it contacts. Selective application is essential. The temporary visual indicator formulated with this herbicide provides a color guide for application of the herbicide so that only those plants that need to be treated are treated and that treated plants are fully sprayed. Herbicides applied in the wind or under conditions created by a fan in a greenhouse are accurately applied when formulated with the temporary visual indicator of the subject invention. The indicator formulated in cropdusting compounds will ensure the delivery of the herbicide is complete and on target. Fertilizers formulated with a temporary visual indicator ensures that the soil to which they are applied is adequately covered.

The temporary indicator of the subject invention can be used in security situations where the colorless state of the indicator conceals the presence of the indicator. The colorless indicator sprayed on a surface is undetected by someone tampering with the surface, but shows signs of being disturbed when the indicator is treated and becomes visible. The person tampering with the surface also picks up indicator of their hands. The indicator can be detected on the hands of the perpetrator after treatment with a disclosure solution allowing the indicator to be visualized. An invisible hand stamp containing the temporary visual indicator which becomes visible upon treatment serves as an alternative to present UV-visible technology.

In a preferred embodiment, phenolphthalein is used as the indicator. Other suitable indicators may be found in U.S. Pat. No. 4,954,544. Phenolphthalein, 3,3-bis[4-hydroxyphenyl]-1-[3H] isobenzofuranone, is colorless in its lactone form, the form present in solutions below pH 8.5. In solutions above pH 9.0, the lactone form of the molecule loses two protons to form an intensely colored red dianion. Sunscreen formulated at a pH above 9.0 is colored pink, or red, by the phenolphthalein. When the pH of the sunscreen drops below pH 8.5 the sunscreen is clear. The continued presence of the phenolphthalein in the sunscreen causes the sunscreen to turn pink should the pH of the sunscreen be raised to a pH above 9.0 again.

The temporary indicator may be formulated into the various products using technology well known in the art. For example, for cosmetic compositions, including sun care products, it may be desirable to encapsulate the indicator. In one embodiment microspheres can be used for this encapsulation. By encapsulating the indicator in microspheres it is possible to advantageously reduce the contact of the visual indicator with skin cells. Preferably, the microspheres would be permeable to the base. Microemulsion as well as suspension and emulsion polymerization techniques for making such microspheres are well-known to those skilled in the art.

In a preferred embodiment, the temporary nature of the visual indicator of the subject invention is due to the selection of a volatile component. As a specific example, when phenolphthalein is used as the visual indicator, a volatile base can be used to raise the pH of the sunscreen containing the phenolphthalein to above 9.0. At that pH, phenolphthalein is in its red dianion form and the sunscreen is colored red or pink by the indicator. On application of the pink sunscreen to skin, the volatile nature of the base causes the base to evaporate or dissipate rapidly. As the base evaporates, the pH of the sunscreen falls below pH 8.5, phenolphthalein returns to its colorless, lactone form and the sunscreen is no longer colored by the indicator. A mild solution of the volatile base can later be sprayed onto the skin to temporarily raise the pH of the sunscreen above pH 9.0 and reactivate the indicator to the red dianion form. Volatile bases appropriate for use in an embodiment of the subject invention include, but are not limited to, monoamines such as ammonia, methyl amine, ethyl amine, isopropyl amine, butyl amine, pentyl amine, hexyl amine and octyl amine, diamines such as ethylene diamine, 1,2-diaminopropane, 1-3-diaminopropane and 1,2-diaminobutane or cyclic amines such as tetrahydropyrrole. Of the volatile bases listed above, ammonia and pentyl amine are currently used as inactive ingredients in marketed drug products.

Although phenolphthalein and a single volatile base are exemplified in the preferred embodiment, other indicators, alone or in combination, and other physical and chemical reactions effecting a color change and providing a temporary visual indication of the location a lotion or like material is applied are also embodied by this invention. Furthermore, more than one volatile component may be formulated into a product containing an indicator. For example, in a sunscreen composition, a first volatile base which evaporates rapidly provides the user a color guide for application, and a second volatile base affecting the same or different indicator which evaporates more slowly signals the user it is time to reapply the composition. As used herein, and throughout the claims, the term "color" includes colors of all shades, hues and intensities visible to the eye. Indicators such as bromthymol blue and thymol blue each operate as indicators within a pH range applicable to the sunscreen embodiment. Both indicators are blue under basic conditions and yellow under neutral conditions. The sunscreen on the skin need not be invisible as long as the color remaining is not objectionable to the user. Color changes of an indicator may be triggered by a variety of physical or chemical reactions. The presence of certain gases, changes in temperature or exposure to UV light may all be used in methods to effect color changes of certain indicators. For example, carbon dioxide in the atmosphere can effect a change in pH of a composition containing a visual indicator. As a specific embodiment the composition can be formulated with distilled water (pH 7.0) or with a small amount of a base such as sodium hydroxide to raise the pH enough above 7.0 so that an indicator can be seen. Then, once the composition is exposed to the open air, carbon dioxide absorption will cause the pH to lower thereby causing the indicator to disappear. Further, the materials and methods of the subject invention can be used to create greenhouse windows that darken automatically as the temperature increases. Boron-amine complexes will dissociate at elevated temperatures. The free amine molecules increase the pH of the surrounding area and trigger a color change of the indicator thereby darkening the windows.

Formulation of the lotions or other materials with the temporary visual indicator of the subject invention can be done utilizing materials and methods well-known and readily available to those skilled in the art. The indicator must be present in an amount sufficient to provide an adequate visual signal when exposed to the base, but should not be present in such a quantity that will affect the qualities of the lotion or other materials in which it is formulated. Suitable compositions of the present invention contain not more than 10% by weight and preferably from 0.001% to about 2% by weight of the indicator. Bases need to be present in an amount sufficient to change the pH of the entire composition to a level that will affect the indicator and be present in an amount sufficient to maintain that pH for an adequate time after the lotion is applied. The base must not be present, however, in amounts that cause the pH of the lotion to be so high that it damages the areas to which the lotion and/or base is applied. Volatile bases are selected with respect to their rate of evaporation. All bases must be selected with regard to their acceptability as components of pharmaceutical compounds and with respect to their toxicity.

Following are examples which illustrate procedures, including the best mode, for practicing the invention. These examples should not be construed as limiting. All percentages are by weight and all solvent mixture properties are by volume unless otherwise noted.

EXAMPLE 1

Indicator Sunscreen Lotion Formulation

The indicator sunscreen lotion of the subject invention may be formulated using commercial sunscreen products as follows:

| | |
|---|---|
| Commercially available sunscreen product (Treasury Brand SPF-4) | 50 ml |
| Pheolphthalein | 100 mg |
| 1,3 diaminopropane | 0.5 ml |

EXAMPLE 2

Disclosing Solution for the Indicator Sunscreen Lotion

The disclosing solution of the subject invention may be formulated as follows:

| | |
|---|---|
| 1,3 diaminopropane | 10 ml |
| Water | 90 ml |

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for marking a surface with a temporary visual indicator comprising:

(a) applying an indicator to the surface at a first pH, the indicator being invisible at the first pH and visible at a second pH;

(b) applying a pH-modifying substance to the surface in an amount sufficient to adjust the pH of the indicator to the second pH and which evaporates or degrades, thereby causing the pH to change to said first pH.

2. The method, according to claim 1, wherein said indicator is 3,3-bis[4 hydroxyphenyl]-1-[3H]-isobenzofuranone.

3. The method, according to claim 1, wherein said pH-modifying substance is a volatile base.

4. The method, according to claim 1, wherein said volatile base is a monoamine.

5. The method, according to claim 1, wherein said volatile base is a diamine.

6. The method, according to claim 1, wherein said volatile base is a cyclic amine.

* * * * *